United States Patent
Imran

(10) Patent No.: US 9,750,935 B2
(45) Date of Patent: Sep. 5, 2017

(54) PATCH AND PATCH ASSEMBLY FOR IONTOPHORETIC TRANSDERMAL DELIVERY OF ACTIVE AGENTS FOR THERAPEUTIC AND MEDICINAL PURPOSES

(71) Applicant: InCube Labs, LLC, San Jose, CA (US)

(72) Inventor: Mir A. Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 0 days.

(21) Appl. No.: 14/524,891

(22) Filed: Oct. 27, 2014

(65) Prior Publication Data

US 2015/0045722 A1    Feb. 12, 2015

Related U.S. Application Data

(63) Continuation of application No. 12/898,671, filed on Oct. 5, 2010, now Pat. No. 8,903,485, and a
(Continued)

(51) Int. Cl.
*A61N 1/30*    (2006.01)
*A61M 37/00*    (2006.01)

(52) U.S. Cl.
CPC ............... *A61N 1/30* (2013.01); *A61M 37/00* (2013.01); *A61M 2037/0007* (2013.01)

(58) Field of Classification Search
CPC . A61M 2037/0007; A61M 37/00; A61N 1/30; A61N 1/303
(Continued)

(56) References Cited

U.S. PATENT DOCUMENTS 3,491,187 A    1/1970    Ely
4,325,367 A    4/1982    Tapper
(Continued)

FOREIGN PATENT DOCUMENTS

CN    1606461 A    4/2005
CN    101036825 A    9/2007
(Continued)

OTHER PUBLICATIONS

Second Office Action dated Aug. 31, 2015 in Chinese Application No. 201280023328.4.
(Continued)

*Primary Examiner* — Kevin C Sirmons
*Assistant Examiner* — Deanna K Hall
(74) *Attorney, Agent, or Firm* — Mahamedi IP Law LLP; Joel Harris

(57) ABSTRACT

Embodiments of the invention provide patch assemblies for iontophoretic transdermal delivery of therapeutic agents. An embodiment provides a patch assembly comprising a conformable patch for delivery of the agent and having a tissue contacting side including an adhesive. The housing has a bottom surface for engaging a non-tissue contacting side of the patch, a current source such as a battery and a controller for controlling the delivery of the agent. The housing has sufficient flexibility such that when it is engaged with the patch to form the patch assembly and the patch is adhered to a target site on the patient's skin, the assembly has sufficient flexibility to deform with movement of the patient's skin to remain sufficiently adhered to the skin over an extended period of time to transdermally deliver a desired dose of the agent. Embodiments of the assembly may used to deliver a variety of therapeutic agents.

28 Claims, 10 Drawing Sheets

Related U.S. Application Data continuation-in-part of application No. 12/537,243, filed on Aug. 6, 2009, now Pat. No. 8,190,252.

(60) Provisional application No. 61/249,247, filed on Oct. 6, 2009.

(58) Field of Classification Search
USPC .......................................................... 604/20
See application file for complete search history.

(56) References Cited

U.S. PATENT DOCUMENTS

| | | | |
|---|---|---|---|
| 4,731,049 A | 3/1988 | Parsi | |
| 4,734,090 A | 3/1988 | Sibalis | |
| 4,764,164 A | 8/1988 | Sasaki | |
| 4,886,489 A | 12/1989 | Jacobsen et al. | |
| 5,207,752 A | 5/1993 | Sorenson et al. | |
| 5,310,404 A | 5/1994 | Gyory et al. | |
| 5,322,502 A | 6/1994 | Theeuwes et al. | |
| 5,328,453 A | 7/1994 | Sibalis | |
| 5,331,979 A | 7/1994 | Henley | |
| 5,385,543 A | 1/1995 | Haak et al. | |
| 5,503,632 A | 4/1996 | Haak | |
| 5,605,536 A | 2/1997 | Sibalis | |
| 5,634,899 A | 6/1997 | Shapland et al. | |
| 5,693,024 A | 12/1997 | Flower | |
| 5,797,867 A | 8/1998 | Guerrera et al. | |
| 5,830,175 A * | 11/1998 | Flower ................. | A61N 1/0436 604/20 |
| 5,928,185 A | 7/1999 | Muller et al. | |
| 5,983,130 A | 11/1999 | Phipps et al. | |
| 6,018,679 A | 1/2000 | Dinh et al. | |
| 6,018,680 A | 1/2000 | Flower | |
| 6,019,877 A | 2/2000 | Dupelle et al. | |
| 6,064,908 A | 5/2000 | Muller et al. | |
| 6,223,076 B1 | 4/2001 | Tapper | |
| 6,330,471 B1 | 12/2001 | Higo et al. | |
| 6,512,950 B2 | 1/2003 | Li et al. | |
| 6,553,255 B1 | 4/2003 | Miller et al. | |
| 6,689,275 B1 | 2/2004 | Gupta | |
| 6,726,920 B1 | 4/2004 | Theeuwes et al. | |
| 6,731,965 B2 | 5/2004 | Menon et al. | |
| 6,779,468 B1 | 8/2004 | Gupta | |
| 7,137,975 B2 | 11/2006 | Miller et al. | |
| 7,340,297 B2 | 3/2008 | Tamarkin et al. | |
| 7,375,139 B2 | 5/2008 | Aldred | |
| 7,437,189 B2 | 10/2008 | Matsumura et al. | |
| 7,496,401 B2 | 2/2009 | Bernabei | |
| 7,522,954 B2 | 4/2009 | Tedoldi | |
| 7,548,778 B2 | 6/2009 | Roy | |
| 7,558,625 B2 | 7/2009 | Levin et al. | |
| 7,590,444 B2 | 9/2009 | Tanioka | |
| 7,593,770 B2 | 9/2009 | Lerner | |
| 7,611,481 B2 | 11/2009 | Cleary et al. | |
| 7,816,404 B2 | 10/2010 | McCall, Jr. | |
| 8,190,252 B2 | 5/2012 | Imran | |
| 8,348,922 B2 | 1/2013 | Imran | |
| 8,417,330 B2 | 4/2013 | Imran | |
| 8,423,131 B2 | 4/2013 | Imran | |
| 8,744,569 B2 | 6/2014 | Imran | |
| 8,903,485 B2 * | 12/2014 | Imran ....................... | A61N 1/30 604/20 |
| 8,961,492 B2 | 2/2015 | Imran et al. | |
| 9,008,765 B2 | 4/2015 | Imran | |
| 2003/0018296 A1 | 1/2003 | Riddle | |
| 2003/0060798 A1 | 3/2003 | Fischer et al. | |
| 2003/0199808 A1 | 10/2003 | Henley et al. | |
| 2004/0138646 A1 | 7/2004 | Walla | |
| 2005/0020487 A1 | 1/2005 | Klaus et al. | |
| 2005/0085751 A1 | 4/2005 | Daskal et al. | |
| 2005/0165393 A1 | 7/2005 | Eppstein | |
| 2005/0209565 A1 | 9/2005 | Yuzhakov | |
| 2005/0213286 A1 | 9/2005 | Michel et al. | |
| 2005/0238704 A1 | 10/2005 | Zumbrunn et al. | |
| 2005/0273046 A1 | 12/2005 | Kwiatkowski et al. | |
| 2006/0025715 A1 | 2/2006 | Henley et al. | |
| 2006/0216339 A1 | 9/2006 | Ambron et al. | |
| 2006/0229549 A1 | 10/2006 | Hause et al. | |
| 2006/0258973 A1 | 11/2006 | Volt | |
| 2007/0065521 A1 | 3/2007 | Venkataraman et al. | |
| 2007/0066934 A1 | 3/2007 | Etheredge et al. | |
| 2007/0083185 A1 | 4/2007 | Carter | |
| 2007/0083186 A1 | 4/2007 | Carter et al. | |
| 2007/0224253 A1 | 9/2007 | Franklin | |
| 2008/0027369 A1 | 1/2008 | Carter et al. | |
| 2008/0058699 A1 | 3/2008 | Hause et al. | |
| 2008/0058700 A1 | 3/2008 | Hause et al. | |
| 2008/0081051 A1 | 4/2008 | Sabin et al. | |
| 2008/0114282 A1 | 5/2008 | Carter | |
| 2008/0154178 A1 | 6/2008 | Carter et al. | |
| 2008/0287497 A1 | 11/2008 | Anderson et al. | |
| 2009/0036821 A1 | 2/2009 | Lai | |
| 2009/0062720 A1 | 3/2009 | Anderson et al. | |
| 2009/0124572 A1 | 5/2009 | Nelson | |
| 2009/0163597 A1 | 6/2009 | Goto et al. | |
| 2009/0171313 A1 | 7/2009 | Yamamoto et al. | |
| 2009/0221985 A1 | 9/2009 | Bukshpan et al. | |
| 2009/0254018 A1 | 10/2009 | Nakayama | |
| 2009/0259176 A1 | 10/2009 | Yairi | |
| 2009/0264855 A1 | 10/2009 | Phipps et al. | |
| 2009/0281475 A1 | 11/2009 | Nisato et al. | |
| 2009/0299264 A1 | 12/2009 | Matsumura et al. | |
| 2009/0299267 A1 | 12/2009 | Durand | |
| 2010/0204637 A1 | 8/2010 | Imran | |
| 2010/0331759 A1 | 12/2010 | Imran | |
| 2010/0331810 A1 | 12/2010 | Imran | |
| 2010/0331811 A1 | 12/2010 | Imran | |
| 2011/0009805 A1 | 1/2011 | Imran | |
| 2011/0082411 A1 | 4/2011 | Imran | |
| 2012/0232464 A1 | 9/2012 | Imran | |
| 2013/0023815 A1 | 1/2013 | Imran | |
| 2013/0023850 A1 | 1/2013 | Imran | |
| 2015/0122253 A1 | 5/2015 | Imran | |

FOREIGN PATENT DOCUMENTS

| | | | |
|---|---|---|---|
| EP | 0090425 A1 | 10/1983 | |
| JP | 1991-045272 | 2/1991 | |
| JP | 2004-508148 | 3/2004 | |
| JP | 2006-0345931 | 12/2006 | |
| JP | 2007-237002 | 9/2007 | |
| JP | 2012-517321 | 2/2010 | |
| WO | WO 96/10442 * | 4/1996 | ............. A61N 1/303 |
| WO | WO 2011/044175 A2 | 4/2011 | |

OTHER PUBLICATIONS

First Office Action dated Apr. 30, 2015 in Chinese Application No. 201280023328.4, Sep. 5, 2016.
European Extended Search Report dated Oct. 10, 2014 in EP Application 12760602.8.
International Preliminary Report on Patentability mailed Aug. 25, 2011 in PCT/US2010/023112.
International Preliminary Report on Patentability mailed Aug. 25, 2011 in PCT/US2010/023744.
International Search Report and Written Report and Notice of Transmittal of same mailed Feb. 25, 2011 in PCT/US2010/040109.
International Search Report and Written Opinion and Notice of Transmittal of same mailed Jun. 24, 2011 in PCT/US2010/051541.
International Search Report and Written Opinion and Notice of Transmittal of Same mailed Sep. 27, 2010 in PCT/US2010/023112.
Murhty et al. "Irontophoresis: Transdermal Delivery of Iron Iontophoresis," J. Pharm. Sci., 98(8): 2670-2676 (Aug. 2009).
Examination Report mailed Aug. 13, 2013 in Australian Application No. 2010213975.
McLaughlin, G.W., et al., "Biphasic Transdermal Iontophoretic Drug Delivery Platform," Conf. Proc. IEEE Eng. Med. Biol.Soc. Aug. 2011: 2011:1225-8.
International Search Report and Written Opinion dated Oct. 31, 2012 as issued in corresponding application PCT/US2012030633.

(56) References Cited

OTHER PUBLICATIONS

International Preliminary Report on Patentability mailed Jan. 12, 2012 in PCT/US2010/040109.
International Preliminary Report on Patentability dated Apr. 19, 2012 as issued in related International application PCT/US2010/051541.
European Search Report dated Jan. 31, 2014 in Application No. 10741574.7.
Office Action mailed Jul. 19, 2013 in Chinese Application No. 1080013328.7.
Office Action dated Feb. 4, 2014 in Japanese Application No. 2011-550168.
Office Action dated Jul. 1, 204 in Japanese Application No. 2011-550168.

* cited by examiner

PATCH AND PATCH ASSEMBLY FOR IONTOPHORETIC TRANSDERMAL DELIVERY OF ACTIVE AGENTS FOR THERAPEUTIC AND MEDICINAL PURPOSES

RELATED APPLICATIONS

This application is a continuation of U.S. patent application Ser. No. 12/898,671 filed Oct. 5, 2010 entitled "Patch And System For Iontophoretic Transdermal Delivery Of Active Agents For Therapeutic And Medicinal Purposes", issued as U.S. Pat. No. 8,903,485, which is a non-provisional filing that claims the benefit of U.S. Provisional Patent Application Ser. No. 61/249,247 filed Oct. 6, 2009, entitled "Patch And System For Iontophoretic Transdermal Delivery Of Active Agents For Therapeutic And Medicinal Purposes." Said U.S. Ser. No. 12/898,671 is also a continuation in part of U.S. patent application Ser. No. 12/537,243 filed Aug. 6, 2009, entitled "Iontophoretic System For Transdermal Delivery Of Active Agents For Therapeutic And Medicinal Purposes," issued as U.S. Pat. No. 8,190,252. The aforementioned applications are hereby incorporated by reference herein in their entirety for all purposes.

FIELD OF THE INVENTION

Embodiments described herein relate to patches and systems for iontophoretic transdermal delivery of various therapeutic agents. More specifically, embodiments described herein relate to patches and systems for iontophoretic transdermal delivery of various iron containing compounds.

BACKGROUND

Iontophoresis is a non-invasive method of propelling high concentrations of a charged substance, known as the active agent, transdermally by repulsive electromotive force using a small electrical charge. This method has been used for the transdermal delivery of various compounds including therapeutic agents. Traditionally, direct current has been used to provide the driving current for iontophoresis. However there are a number of shortcomings associated with the use of direct current including limitations on the total amount of current that can be delivered over time without causing injury to the skin, as well as the build up of capacitive charge in the skin layer which can oppose the electromotive driving forces thus reducing the rate and total amount of compound delivered over time. Also, direct current can cause a local anesthetic effect to the skin resulting in burns and other thermal damage to the skin because the user doesn't feel the injury to the skin occurring at the time. Thus there is need for improved methods for delivering various therapeutic agents using transdermal iontophoresis.

BRIEF DESCRIPTION OF THE DRAWINGS

FIG. 6a shows a top view, FIG. 6b shows a bottom view.

DETAILED DESCRIPTION OF THE INVENTION

Figure 1:
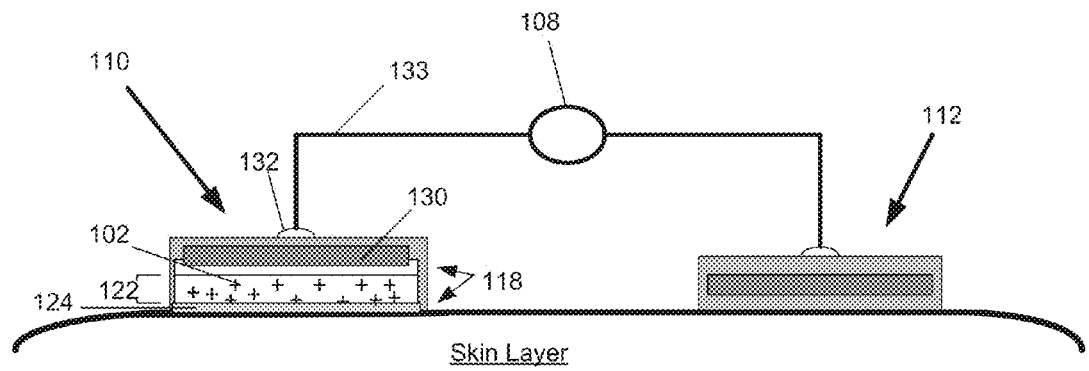
FIG. 1 illustrates an iontophoretic system for transdermal delivery of an active agent, according to one or more embodiments.

Embodiments described herein provide for an iontophoretic system for transdermal delivery of drugs and other therapeutic agents. As used herein, the term transdermal refers to the delivery of a compound, such as a drug or other biological agent, through one or more layers of the skin (e.g., epidermis, dermis, etc). Iontophoresis is a non-invasive method of propelling high concentrations of a charged substance, known as the active agent, transdermally using electrical current applied at the skin layer. The active agent can include a drug or other therapeutic agent or biological compound.

More specifically, embodiments described herein include a system for transdermal delivery of active agents for therapeutic and medicinal purposes. The system includes a power source and at least two electrode assembles. The power source provides an output current that alternates between a maximum current value and a minimum current value; a pair of electrode assemblies. Each electrode assembly is configured to be held in contact with a skin layer of a user. Additionally, each electrode assembly includes an electrode that is coupled to the power source to receive the output current from the power source. At least one of the electrode assemblies in the pair includes a medium that carries an active agent having a charge, the medium being provided on the at least one electrode assembly to enable the output current to repel the active agent into the skin layer for a duration in which the output current has a polarity that is the same as a polarity of the active agent.

According to one or more embodiments, an output current such as described is a charged balanced alternating current (AC) output. The charged balance AC output means over a given duration, the amount of current delivered at each polarity is substantially equivalent. As used herein substantially equivalent means that two values are within 80% of one another, and more preferably within 90% or 99% waveform.

In another aspect, embodiments of the invention provide an iontophoretic transdermal delivery system which include a skin conformable patch and an electronics assembly. The patch includes first and second electrode assemblies which include electrodes. One or both of electrode assemblies can include a pair of tissue contacting ring shape electrodes concentrically spaced or otherwise arranged to reduce edge effects.

The electronics assembly includes a housing which may be configured to be detachably coupled to the conformable patch via one or more detachment elements. The housing can include a curved shaped contour configured to correspond to the contour of the skin surface on the portion of the body where the housing and patch are placed (e.g., the contour of the arm, leg or abdomen). The housing itself can be conformable so as to at least partially conform to the contour of the skin surface where the housing and patch are placed.

The housing will also typically include a current source such as an electrochemical battery and a microprocessor or other controller. The battery can include various electrochemistries known in the art and can be rechargeable. Also, it may have a selectable capacity to deliver current to skin for transdermal delivery of the therapeutic agent for periods ranging from 2 to 24 hours or even longer. Other current sources are also contemplated such as various storage capacitors. The battery may be positioned in a cavity within the housing.

The controller can include a microprocessor or other electronic controller for controlling one or more aspects of the iontophoretic delivery of the agent to the skin. The controller can also include an integrated or separate power controller for controlling the delivery of current to the skin. One or both of the controllers can be coupled to an H-bridge for limiting the delivery of current to the skin.

Single Point Disbursement

FIG. 1 illustrates an iontophoretic system for transdermal delivery of an active agent, according to one or more embodiments. A system 100 is shown in a deployed (i.e. operational) state, and comprises a pair of active electrode assemblies 110, 112 and alternating power source 108 that combine to enable the transdermal delivery of a medicinal or therapeutic ("active") agent 102 into a user's tissue. Therapeutic agent 102 can comprise one or more drugs or other therapeutic agents. In the deployed state, the pair of electrode assemblies 110, 112 are positioned on the exterior skin layer of the user. In one embodiment, the alternating power source 108 forces the agent 102 to be dispensed from one of the electrode assemblies in the pair (shown as electrode assembly 110 in FIG. 1). More specifically, the active agent 102 is selected to have an ionic charge, and the alternating power source 108 is connected to electrode assembly 110 to repel the active agent 102 into the skin layer of the user at instances when the alternating power source has the same polarity as the active agent. As such, the driving mechanism that causes the active agent 102 to dispense into the skin layer is intermittent and alternating (to match the output of the power source 108).

With specific reference to FIG. 1, the power source 108, electrode assemblies 110, 112 and the user's (also referred to herein as patient) skin layer or tissue form a circuit to enable delivery of the active agent from at least one of the electrode assemblies. More specifically, FIG. 1 illustrates a single disbursement configuration in which the first electrode assembly 110 contains the active agent, and the second electrode assembly 112 serves as a return without the active agent. In the configuration shown, the second electrode assembly 112 serves as the return for completing the circuit with power source 108 and the first electrode assembly 110. For a duration, the output current is provided a polarity that matches that of the charge of the active agent. The presence of the output current, flowing via the circuit formed by the other electrode assembly and the power source 108, results in the charged active agent being repulsed from the electrode assembly 110 into the skin layer of the user. Thus, in a configuration shown by FIG. 1, the first active electrode assembly 110 is equipped with the active agent 102, and the power source 108 directs the active agent from the first electrode assembly 110 into the skin layer when the polarity of the output current matches that of the charge of the active agent.

As described below, the power source 108 may vary the output of the current output to alternate durations in which the active agent is delivered. In one embodiment, the power source 108 varies the output current between a maximum current value (coinciding with a delivery duration) and a minimum current value (coinciding with non-delivery duration). The minimum current value corresponds to either no current output, or a reverse current output. As described elsewhere, the reverse current output may serve as a retention mechanism that actively precludes the active agent from diffusing into the skin layer (e.g., due to electrostatic attractive forces). Thus, a delivery duration coincides with a duration in which an output current from the power source 108 has polarity to match that of the active agent. A non-delivery duration coincides with either an output current from the power source that is opposite in polarity to that of the active agent, or to a duration that coincides with substantially no current output.

In a system such as described with FIG. 1, some embodiments provide for the delivery/non-delivery durations to be symmetrical or equal. For example, delivery/non-delivery durations may each last x milliseconds, seconds, or minutes, to match, for example, symmetrical waveforms of the output (e.g. sinusoidal, square wave etc.). In other embodiments, the delivery/non-delivery durations are asymmetrical or unequal. For example, the delivery duration may last several minutes, and the non-delivery duration may last only seconds or otherwise be less than the delivery duration. The delivery/non-delivery durations may repeat, or pass through only a single cycle (i.e., one delivery duration and one non-delivery duration).

Each electrode assembly 110, 112 includes an electrode 130 and a contact thickness 118. The contact thickness 118 of each electrode assembly 110, 120 may be in form of a patch fabricated from layers of elastomeric or other flexible polymer material. The contact thickness 118 may include, for example, adhesives for enabling the respective electrode assemblies 110, 112 to be deployed on the skin layer of the user and to remain adhered over an extended period of time during movement of the skin. Likewise, the electrode 130 corresponds to one or more elements or layers that extend the conductive path from the alternating power source to the contact thickness and/or skin layer. In one embodiment, a connector 132 connects the electrode 130 to leads 133 of powers source 108. The electrode 130 corresponds to a metal layer or element(s) (e.g. wiring, contact elements etc.) that extends or connects to the connector 132. The electrode 130 may comprise a separate layer from the contact thickness 118, which includes a medium 122 for carrying the active agent 102. However, in some variations, the electrode 130 includes elements, such as particles or contact elements that are integrated or provided with the contact thickness 118. In one implementation, the electrode 130 is comprised of conductive material, such as metal (e.g. silver) or conductive carbon material (graphite sheets). In an embodiment depicted by FIG. 1, electrode 130 is a conductive layer that overlay the contact thickness 118. As described below, the contact thickness 118 includes thicknesses for dispersing the active agent 102, as well as material to enable the electrode assembly to be adhered to skin, for example, a skin adhesive known in the art such as those used on self adhering bandages. In many embodiments, the active agent is dissolved in an aqueous or other carrier solution, for example, isopropyl alcohol, DMSO and like compounds.

As previously mentioned, in an embodiment of FIG. 1, only one of the electrode assemblies in the pair (shown as electrode assembly 110) is used to deliver the active agent 102 into the user's skin. The medium 122 of the first electrode assembly 110 provides a reservoir or retainer that contains the active agent, for example, in embodiments where the active agent is dissolved in a carrier solution. More specifically, the medium 122 of the contact thickness 118 includes a tissue contacting porous layer 124, which can either be separate or part of a reservoir. The porous layer 124 can be configured to absorb the carrier solution from the reservoir and in turn, wick the solution into contact with the skin (e.g. by capillary action). The porosity of the porous layer 124 may be selected based on various parameters. For example, the porosity may be selected based on the concentration or transport characteristics of the active agent. More specifically, for example, high porosities can be selected for higher molecular weight therapeutic agents and/or therapeutic agents solutions having greater viscosity. Suitable porous materials for porous layer 124 can comprise compressed cotton or other fibrous mesh such as meshes made from various polymer fibers.

The electrode assemblies 110, 112 can be constructed as disposable or reusable. If disposable, the electrode assembly 110 (carrying the active agent) is manufactured or retailed to include the active agent in the medium 122. For reusable embodiments of assemblies 110 and 112, an embodiment provides that the electrode assembly 110 includes an intake conduit and optional self-sealing port that enables the active agent 102 to be dispersed in the medium 122 for delivery. In one embodiment, the self-sealing port is formed from silicone or other elastomeric material, so as to enable the electrode assembly 110 to be filled with the active agent.

The alternating power source 108 may correspond to a battery, such as a rechargeable Lithium-Ion battery pack. As an alternative, the alternating power source 108 may, include or provide an interface, to another power source, such as a solar cell. Circuitry (such as described with FIG. 4) may be used to convert the direct-current (DC) power output to an alternating signal of a specified waveform. As mentioned elsewhere, the specified waveform may be short (e.g. milliseconds), long (minutes), symmetrical (delivery/non-delivery are equal), or asymmetrical (delivery/non-delivery are now equal).

In various embodiments, the electrode assemblies 110, 112 and the alternating power source 108 may be provided in connection with one or more housing segments. For example, the power source 108, electrode assemblies 110, 112, and wiring or connectors that interconnect the power source and the electrode assemblies may all be contained by a housing, or combination of integrated housing segments. In this way, the system of electrode assemblies 110, 112 may be provided as a product, device or kit that can be assembled and deployed by the user. The kit may further include instructions for use.

When deployed and made operational, the active agent is selected to have an ionic charge that can be sufficiently repulsed by the presence of current having the same polarity. The active agent is distributed in the medium 122 of the electrode assembly 110. The power source 108 is connected and signaled, resulting in a circuit being formed between the alternating power source 108, electrode assembly 110 containing the active agent, and the electrode assembly 112 providing the return electrode. In the durations when the current has the same polarity as the charge of the active agent, the active agent is repulsed from the medium 122 of the electrode assembly 110 into the skin layer of the user. In the durations when the current has the opposite polarity as the charge of the active agent, the active agent is not repulsed. Thus, the active agent is induced to travel into the skin layer in alternating durations to match the alternating power of the alternating power source 108. The frequency of the alternating power source 108 may vary greatly. In particular, the frequency of the alternating power source may be in the range of milliseconds (e.g. 1/60 seconds) or minutes (e.g. ten minutes).

Among other benefits, the diffusion of the active agent into the skin layer can be completely stopped with the switch in the current polarity. Thus, use of the alternating power source 108 enables the active agent to be stopped from entering the skin layer at alternating instances. This enables, for example, better control of the amount of active agent delivered into the skin layer in a given duration.

Double Point Disbursement

Figure 2:
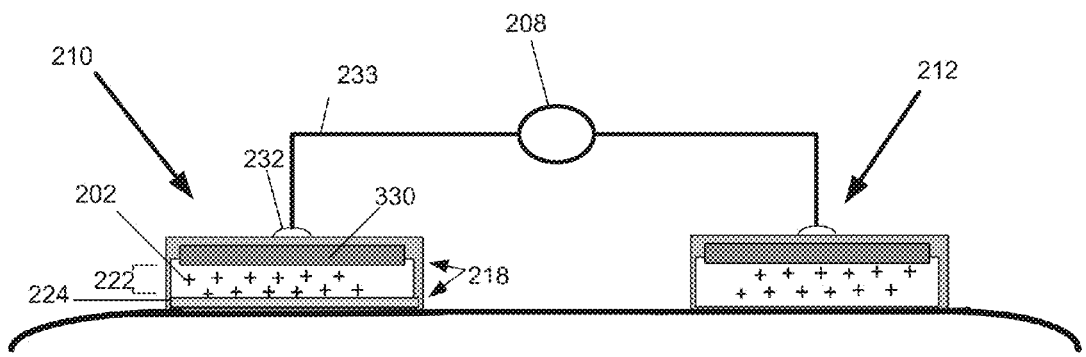
FIG. 2 illustrates an alternative embodiment in which each of a pair of electrode assemblies are equipped to disperse an active agent into the skin layer, under another embodiment.

FIG. 2 illustrates an alternative embodiment in which each of a pair of electrode assemblies are equipped to disperse an active agent into the skin layer, under another embodiment. More specifically, an embodiment of FIG. 2 shows a first and second electrode assembly 210, 212, each of which can include a construction similar to that shown with the first electrode assembly 110 of FIG. 1. Accordingly, the first and second electrode assemblies 210, 212 each include an electrode 230 positioned over or in operative relationship to a contact thickness 218. The contact thickness 218 of each electrode assembly 210, 220 may be in form of a patch fabricated from layers of elastomeric or other flexible polymer material. The contact thickness 218 may include, for example, adhesives for enabling the respective electrode assemblies 210, 212 to be deployed on the skin layer of the user. Likewise, the electrode 230 of each electrode assembly 210, 212 may correspond to one or more metal layer or element(s) (e.g. wiring, contact elements etc.) that extends or connects to a connector 232, which in turn connects that electrode 230 to leads 233 of powers source 208. On each electrode assembly 210, 212, the electrode 230 may comprise a separate layer from the contact thickness 218, which includes a medium 222 for carrying the active agent 202. However, in some variations, the electrode 230 includes elements, such as particles or contact elements, that are integrated or provided with the contact thickness 218. In one implementation, the electrode 230 is comprised of conductive material, such as metal (e.g. silver) or conductive carbon material (graphite sheets).

The medium 222 of the electrode assemblies 210, 212 includes a tissue contacting porous layer 224, which can either be separate or part of a reservoir. Similarly, in an implementation in which one or both of the electrode assemblies 210, 212 are reusable, a self sealing port (not shown) may be included to enable the active agent to be dispersed in the medium 222 for delivery to the skin layer.

As a variation, the electrode assemblies 210, 212 may both be capable of retaining the active agent to dispense, but the electrode assemblies 210, 212 may have differing constructions. For example, the contact layer and amount of active agent 202 each electrode assembly 210, 212 can retain may be different.

In contrast to an embodiment of FIG. 1, the alternating source 208 is electrically connected to cause dispersion of active agent 202 from both electrode assemblies 210, 212 in alternating fashion. In one embodiment, the alternating power source 208 alternates the power signal to each electrode so that the delivery durations form each electrode assembly are the same. Such a configuration enables delivery durations to alternate between electrode assemblies. Among other benefits, alternating the delivery durations between electrode assemblies enables continuous transdermal delivery of Z agents using alternating points in the user's skin, to avoid, for example, skin irritation or saturation.

Similar to prior embodiments of FIG. 1, an embodiment such as that described with FIG. 2 may be constructed as a device or kit that can be assembled and deployed for use by the user. Accordingly, one or more housing segments may be incorporated to integrate the electrode assemblies 210, 212 and/or power source 208.

Figure 3:
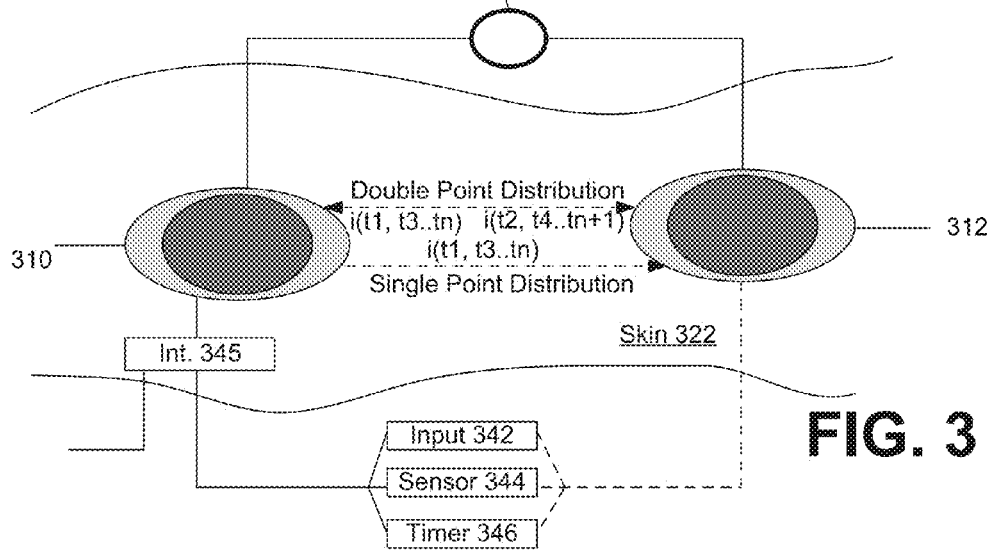
FIG. 3 is a top view of the electrode assemblies deployed on a skin layer of the user.

FIG. 3 is a top view of the electrode assemblies deployed on a skin layer of the user. The electrode assemblies 310, 312 may be implemented to disperse an active agent from one electrode assembly (single point disbursement, such as described with FIG. 1) or from both electrode assemblies 310, 312 (double point disbursement, such as described with FIG. 2). In a single point disbursement configuration, the alternating power source 308 repulses the active agent into the skin 322 (into the paper, as depicted by Z axis) in alternating durations when the supplied current has the same polarity as the charge of the active agent. As mentioned elsewhere, the alternating durations may last milliseconds, seconds, or minutes. The alternating durations may also be asymmetrical or unequal in duration. In a single point disbursement, for example, current is extended from the alternating power source 308 through the contact thickness (see element 118 of FIG. 1) of the first electrode assembly 310, into the skin layer 322, and to the second electrode 312 (serving as the return) to form a circuit with the alternating power source 308. The active agent is thus dispensed from one electrode assembly 310 into the skin layer in alternating durations (durations marked by $t_1, t_3, t_n$) set by the frequency of the current from the power source 108. Significantly, the active agent does not dispense passively in the alternating instances when the polarity of the current is opposite to the charge (i.e. attractive polarity) of the active agent (durations marked by $t_2, t_4, t_{n+1}$). In that instance, the opposite polarity of the current/voltage serves as a retention mechanism of the active agent within the electrode assembly 310.

In a double point disbursement configuration (such as described with an embodiment of FIG. 2), the alternating power source 308 alternates which electrode assembly is directing the active agent into the skin layer 322. In one implementation, for example, both electrode assemblies may carry the active agent, and the active agent is positively charged. At a first duration when the current has a positive polarity, (i) a positively charged active agent in the first electrode assembly 310 is directed into the skin layer, (ii) a positively charged active agent in the second electrode assembly 312 is retained, or precluded from being diffused into the skin layer. In the next duration, when the current has the negative polarity, (i) a negatively charged active agent in the first electrode assembly 310 is retained or precluded from being diffused into the skin layer; and (ii) a positively charged active agent in the second electrode assembly 312 is directed into the skin layer. The timing sequence of the first electrode assembly 310 thus may be described as (i) dispense at durations marked by $(t_1, t_3, t_n)$, and (ii) retain at durations marked by $(t_2, t_4, t_{n+1})$. Likewise, timing sequence of the second electrode assembly 312 may be described as (i) dispense at durations marked $(t_2, t_4, t_{n+1})$ and (ii) retain at durations marked by $(t_1, t_3, t_n)$.

With regard to either the single or double point disbursement configuration, the frequency of the electrode assemblies operation may be measured in milliseconds, seconds or minutes. For example, in a single disbursement embodiment, a drug-on mode of operation may last several minutes, followed by a drug-off mode. The time periods for the drug-on and drug-off states may be the same or different. For example, the drug-on states may last several minutes, but the drug-off state may be much shorter.

According to an embodiment, the electrode assemblies 310, 312 can be used in connection with the following mechanisms to initiate and/or stop use of the electrode assemblies: (i) input from a user input mechanism 342, (ii) input from a sensor 344 or sensor system for detecting a human/physiological condition, and/or (iii) a timer 346. A user input mechanism may correspond to a switch, button or similar mechanism that the user can trigger. The user input mechanism 342 may be used to initiate use of the electrode assemblies 310, 312 once the user places the electrode assemblies on his skin. The user input mechanism 342 may also be used to stop the electrode assemblies at the user's election. For example, the user may deploy the electrode assemblies on his skin layer, then press a button or cause the power source to power the electrodes at a desired time.

The sensor 344 (or sensor system) may correspond to a physiological sensor that triggers the electrode assemblies to operate when the sensor 344 detects a physiological condition. For example, the sensor 344 may correspond to a glucose monitor for diabetics; the glucose conditions trigger sensor 344 to actuate the electrode assemblies.

As an alternative or variation, a system such as described with FIG. 3 may be provided with an interface 345 to enable the power source 308 to be triggered or operated by the output of sensor 344 or other sensor. In this way, a system such as described by various embodiments may be deployed in an environment where the user has one or more pre-existing body sensors to detect various conditions. The interface 345 may include logic or circuitry to enable interpretation of the sensor output from the user's sensor system.

The timer 346 corresponds to a mechanism, implemented by, for example, logic or circuitry, that (i) switches the power source 308 from a state of delivery (i.e. signal current output to the electrode assemblies) to a state of non-delivery through current/voltage output; and/or (ii) switches the power source 308 from a state of non-delivery (i.e. signal reverse current or no current) to a state of delivery. In a typical implementation, the timer 346 may switch the power source 308 into a state in which the current output matches the charge of the active agent for a set duration, then switch the power source to either turn off or output a reverse current.

As an alternative or variation to embodiments described, the sensor 344 or sensor system is configured to trigger electrode assemblies 310, 312 to cease operation when a physiological condition is no longer present. As still another variation, rather than switch off, an embodiment may switch the mode of operation of the electrode assemblies from a drug deliver to a drug-off state. The drug-off state differs from an off state, in that a reverse current may be used to (i) maintain the electrodes in the deployed state, but (ii) retains the active agent with the electrode as a result of the polarity of the current. For example, with reference to an embodiment of FIG. 1, when the sensor 344 detects presence of the physiological condition, the electrode assembly 310 switches on to deliver a type of active agent to address the condition. After the physiological condition is being detected as being treated (either by sensor or timer), the electrode assembly 310 switches into a reverse current state, so that no drug is delivered into the skin layer. Subsequent re-occurrence of the condition may trigger the first electrode assembly 310 into the drug delivery mode again upon the sensor 344 detecting re-occurrence of the physiological condition.

Various embodiments described above provide for alternating current/voltage to drive a charged active agent from an electrode assembly into the skin layer of the user. Embodiments further recognize that a waveform of the alternating current/voltage that is output from the alternating power source may be of consequence as to the operation and application for the transdermal iontophoretic delivery system described by various embodiments. Numerous current output waveforms and applications for using such waveforms are described with FIG. 5A through FIG. 5F.

Applications and Waveforms

Figure 4:
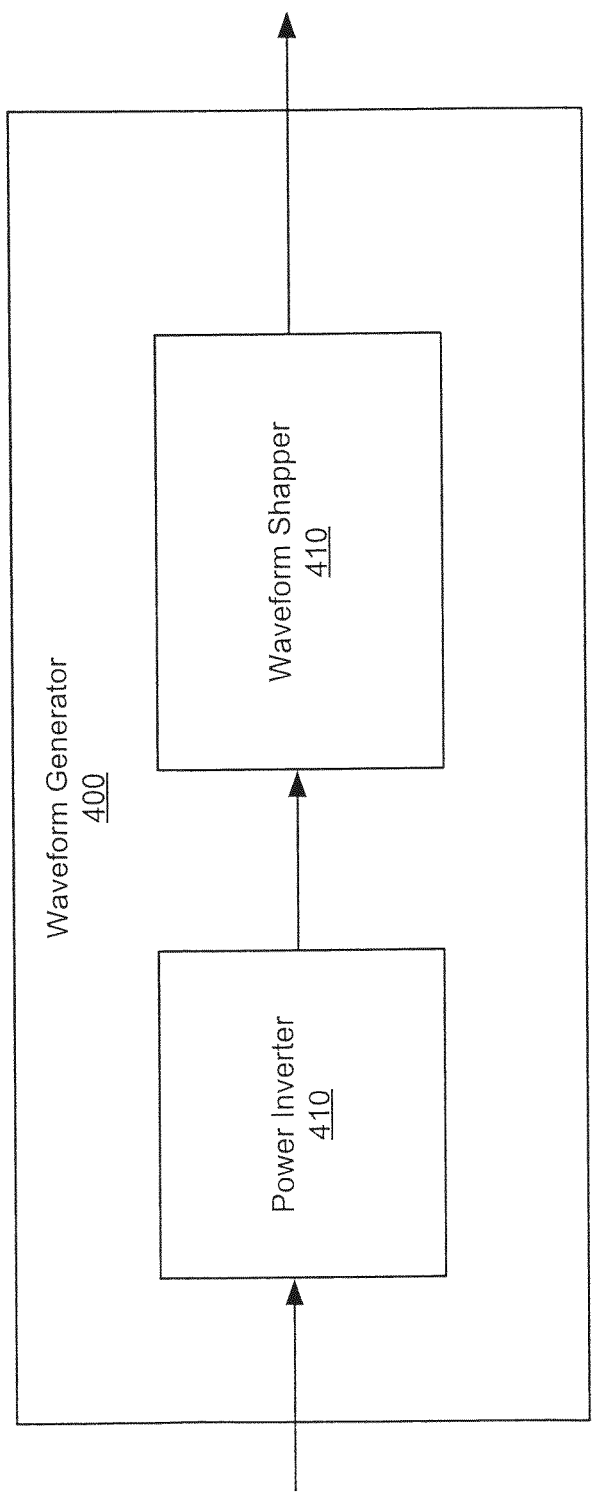
FIG. 4 illustrates an alternating power source for use with embodiments such as described with FIG. 1 though FIG. 3.

FIG. 4 illustrates an alternating power source for use with embodiments such as described with FIG. 1 though FIG. 3. The waveform generator 400 has an input to receive a DC current from a battery (or other power source, such as photovoltaic solar cell) and converts the input into a shaped waveform. Examples of the shaped waveform may be a sinusoidal waveform, a square waveform, a trapezoidal waveform, or other similar waveforms. Some waveforms, such as square waves, in particular, may short or long frequency. Short frequency waveforms may repeat several times per second (e.g. 1/60 seconds), while long frequency waveforms may repeat once over several minutes (e.g. 20 minutes). In generating the waveforms, some embodiments use a voltage that is in range of 1 to 100 volts.

The waveform generator 400 includes power inverter 410 and waveform shaper 420. Power inverter 410 has an input to receive the DC current and an output to transmit an AC current to the waveform shaper. The waveform shaper 420 includes circuitry to shape the AC current to the desired waveform. For example, the waveform shaper 420 may include capacitive or inductive elements in order to obtain the desired shape of the waveform. The shaped waveform is outputted by the waveform generator 400.

FIG. 5A through FIG. 5F illustrates various waveforms or current output variations (over time) that can be used to promote a characteristic of the electrode assemblies operation on a user's skin. Embodiments such as described may be implemented in either a single (see FIG. 1) or double (see FIG. 2) disbursement configuration. In describing an embodiment of FIG. 5A-5F, reference may be made to elements or numerals of FIG. 3 for purpose of illustration. Numerous embodiments described herein provide for waveforms that vary between a given polarity and zero, wherein at polarity, the current causes the active agent to repel in the skin layer. In other embodiments, the waveforms have alternative between positive and negative polarity. In some embodiments, the alternating currents can be delivered to each electrode assembly that is in use (whether or not the electrode assembly has the active agent). By orienting the waveform to alternate in a charged-balance fashion, electrical toxicity or damage to the skin can be reduced or minimized. In other embodiments, an alternating current is used that is oriented towards being balanced in charge, but some asymmetry may exist. However, the amount of asymmetry may be kept below that which causes electrical toxicity to the skin.

The waveforms described below are variable between a minimum and maximum value. Some embodiments, such as described with FIG. 5B, may be alternating in charge value (i.e. include reverse polarity). In such embodiments, the current delivery may be balanced in charge.

Figure 5A:
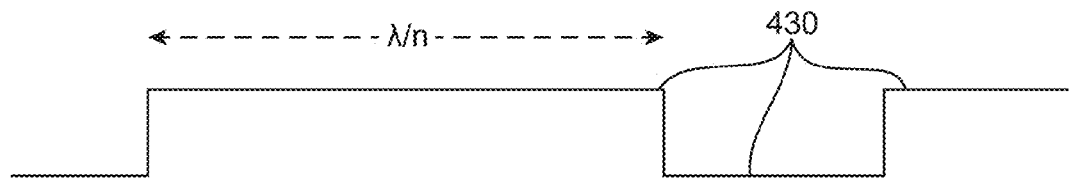
FIG. 5A through FIG. 5F illustrate various waveforms or current output variations that can be used to promote a characteristic of the electrode assemblies operation on a user's skin.

FIG. 5A illustrates a waveform 430 that includes an extended or long drug delivery phase, according to an embodiment. In some embodiments, the skin layer may be assumed to handle only a maximum amount of current in a given duration (max current delivery) (e.g. 80 milliamps per minute). For a given amperage, the duration of the output of the alternating power source may be set to not exceed the max current delivery. The delivery duration may be set to some portion or fraction (e.g. 50% for n=2) of the overall period of the current output $I_1$. For example, in some implementations, the max current delivery ($I_1$) is assumed to be 80 milliamps for one minute. In such an implementation, the delivery duration is set for 20 seconds on 4 milliamp output. Rather than switch to negative polarity, the output of the power source 308 may alternate to no amperage output (rather than switch polarity). While the waveform depicted in FIG. 5A is rectangular, the waveform may have an alternative shape (e.g. sinusoidal, trapezoidal), with the current delivery corresponding to the area under the curve. In the example shown by FIG. 5A, the alternating power source 308 initiates a delivery duration on one electrode, with delivery durations being set by a current that has a polarity that matches that of the charge of the active agent. The current may alternate to zero output, in which the drug delivery is substantially ceased. Thus, the no-delivery duration may coincide with no current output, rather than reverse current.

Figure 5B:
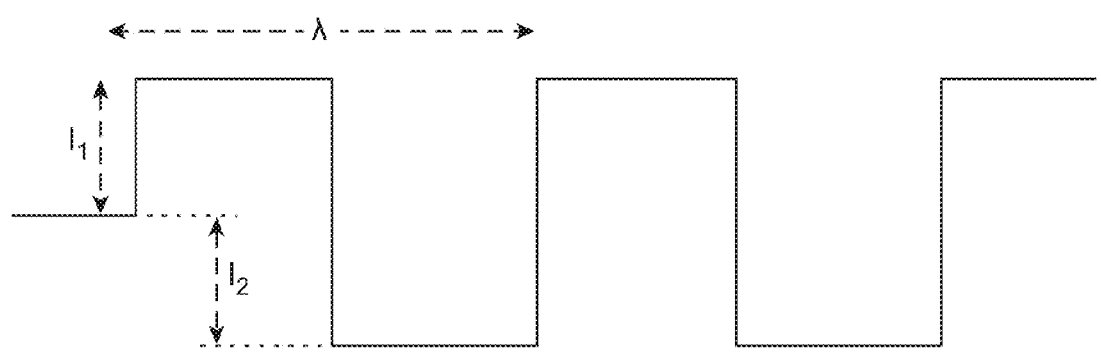

FIG. 5B illustrates another embodiment in which the alternating power signal outputs a symmetrical square wave. FIG. 5B (and other waveforms illustrated herein) illustrate use of charged balance alternating currents. For example, symmetrical waveforms in polarity may be considered as charged balance. Depending on the application, the cycle may be long (e.g. 20 minutes) or short (1/60 seconds). The delivery duration may correspond to half of the period of the waveform. In the implementation shown, a reverse current is used to in the non-delivery duration, to actively prevent agent delivery to the skin layer.

Figure 5C:
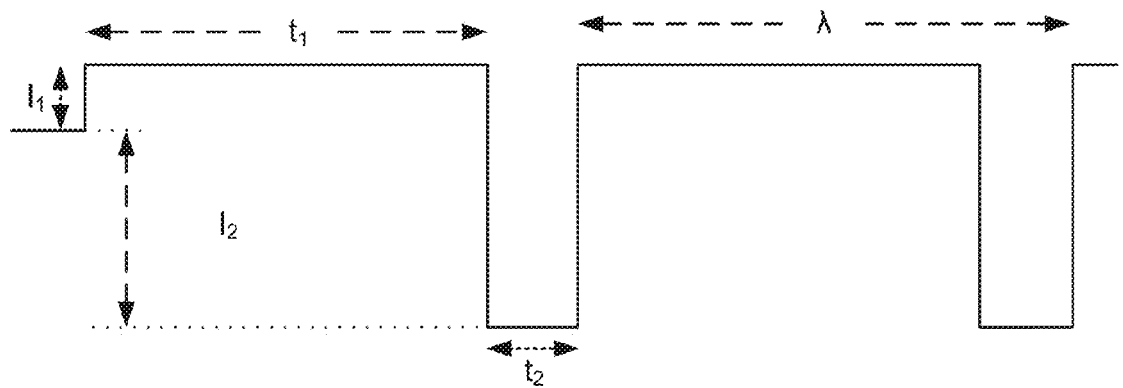

FIG. 5C illustrates another embodiment in which the alternating power signal outputs an asymmetrical square wave, in that the delivery duration is different than the non-delivery duration. More specifically, the asymmetrical square wave may include longer delivery durations ($t_1$), followed by short(er) rest durations ($t_2$). The rest durations may correspond to periods of no current, or as shown, reverse current ($I_2$). In one application, the rest duration enable the skin layer to recuperate from the drug delivery in the prior duration (e.g., to dissipate any heat, concentration of ions, or other by products resulting from the delivery of current). As an alternative or variation, the rest period may follow a period where no current is applied to the skin layer, so as to enable the skin layer to recuperate from application of current.

Figure 5D:
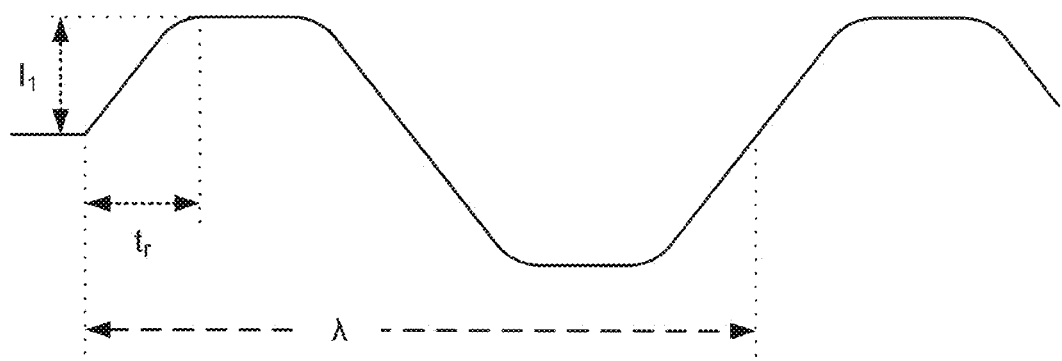

FIG. 5D illustrates another embodiment in which the alternating power signal is trapezoidal, so as to include a ramp-up and/or ramp-down. As depicted, $I_1$ is the maximum current output generated from the power source 308. The ramp-up period extends for a duration $t_r$, selected for reasons that include enabling the user to physically accustom to the application of current and/or active agent. The period may be long, to enable the ramp-up duration to be effective. In an embodiment, a ramp-down period may optionally be implemented.

Figure 5E:
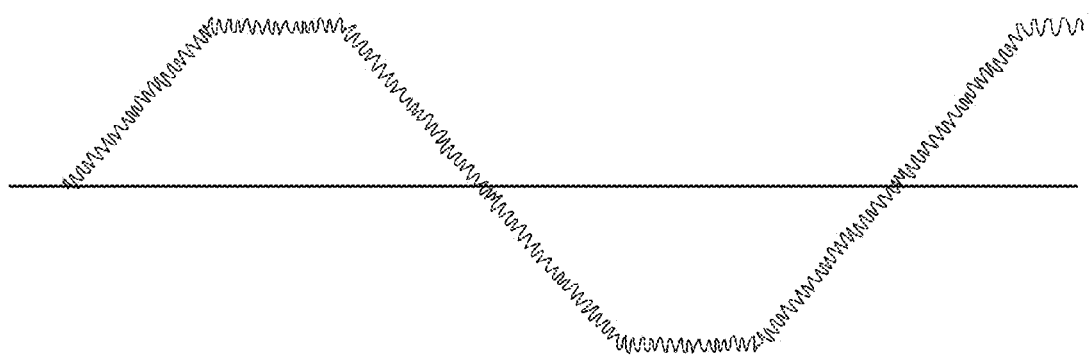
Figure 5F:
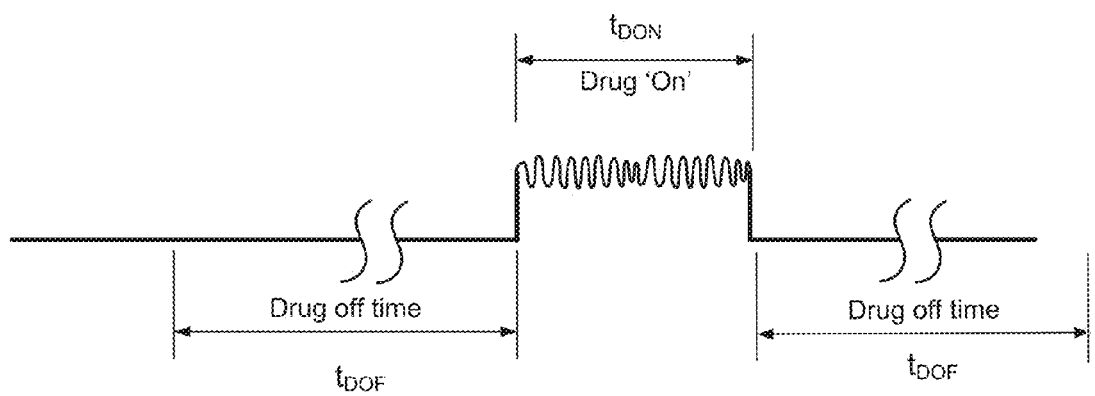
Figure 6A:
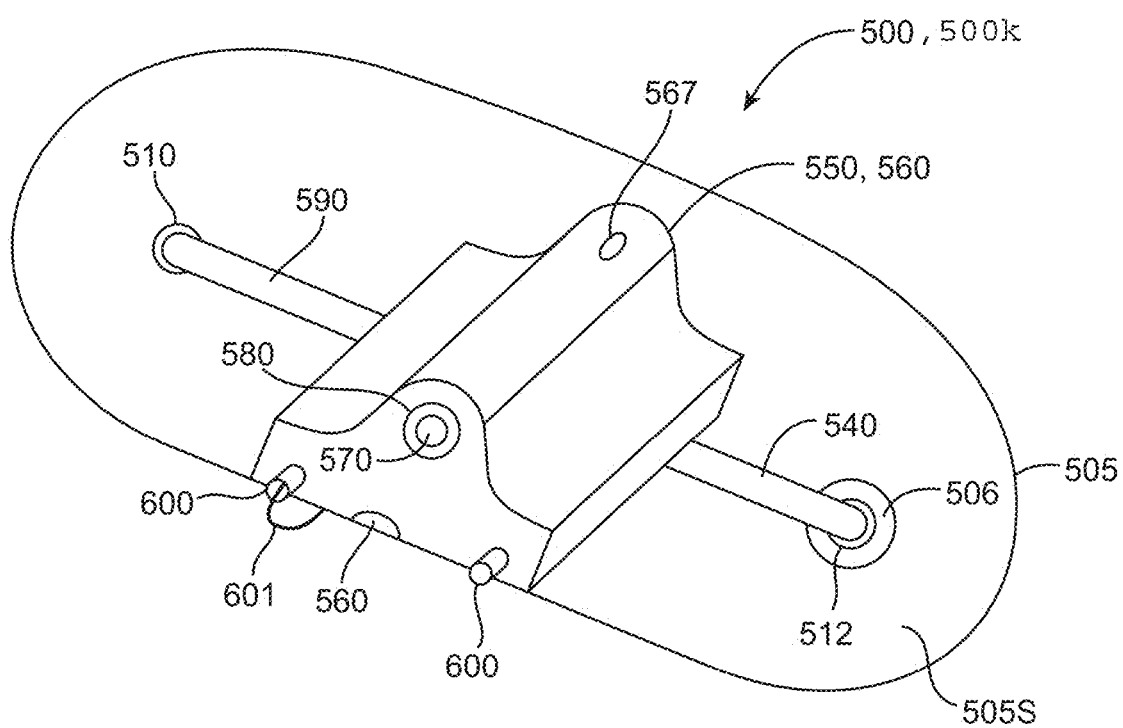
FIGS. 6a and 6b are perspective views showing an embodiment of a system/patch assembly for iontophoretic transdermal delivery of an active agent including a patch and an electronics assembly.
Figure 6B:
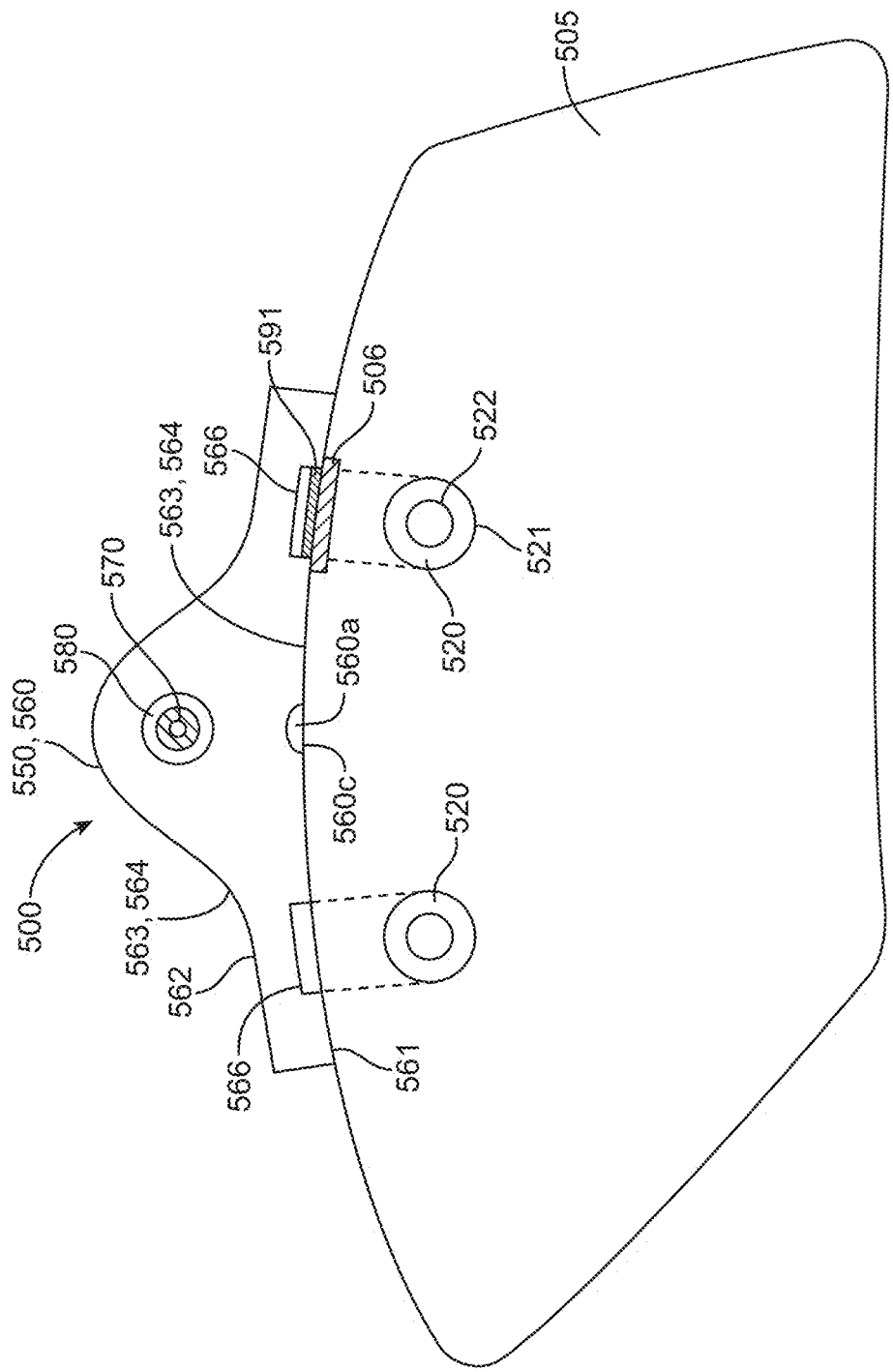
Figure 6C:
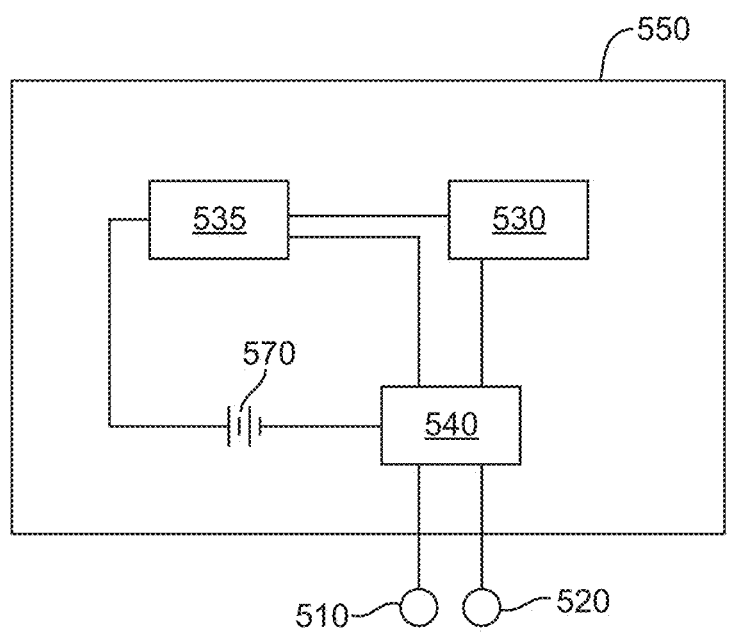
FIG. 6c is a block diagram of an embodiment of the electronics assembly including a controller, current source and current switching device.
Figure 7A:
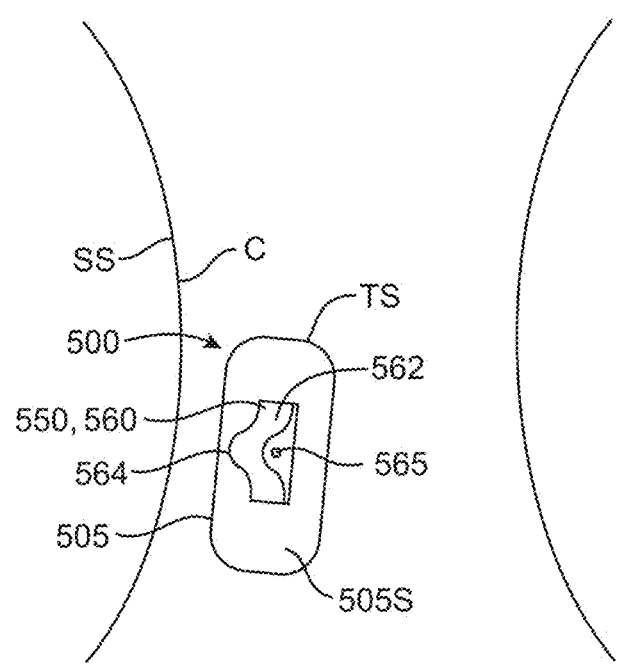
FIG. 7a is a perspective view showing placement of the embodiment of FIG. 6a and FIG. 6b on an example site on the skin of a user.
Figure 7B:
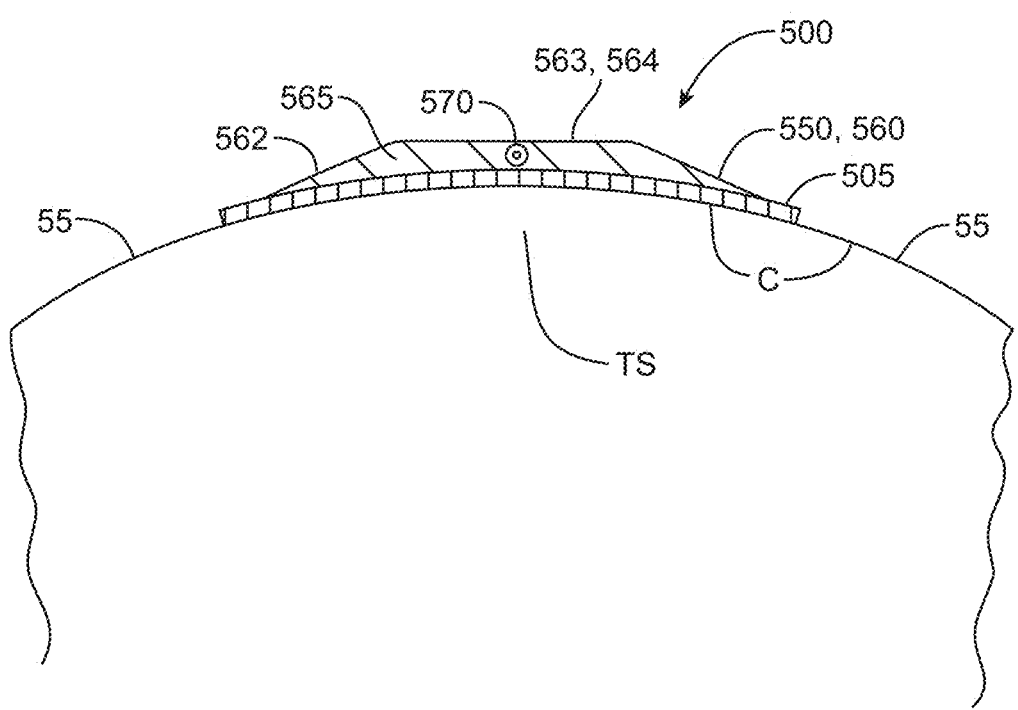
FIG. 7b is a lateral view showing an embodiment of a patch assembly having a curved contour positioned at a tissue site having a curved contour.

FIG. 5E and FIG. 5F illustrate alternative waveform variations in which high-frequency oscillations are superimposed on a base waveform. The base waveform may have a period that lasts seconds or minutes, corresponding to output current to the electrode assemblies ranging from a maximum (e.g. 4 MA) to no current and/or reverse current. The high-frequency oscillations reflect small variations in the current value at instances in the period. The period of the high-frequency oscillations may be one or more magnitudes shorter than that of the base waveform. As an example, the base waveform may have a period ranging seconds to minutes, and the high-frequency oscillations of the waveform may have a period that ranges between milliseconds and seconds. The effect of the high-frequency oscillations is to reduce the effects of the capacitive charge in the skin layer in receiving the active agent. The high frequency oscillations may also be used to facilitate transport of the active agent through the skin including the stratum corneum by causing oscillations in the movement of the active agent as it travels through the skin so as to find pathways of least resistance through skin. In such embodiments, the high frequency oscillations may be adjusted to enhance this effect through use of modeling (e.g., pharmacokinetic modeling) and/or the patients age, skin type and skin location.

The base waveform may be selected for considerations such as described in prior embodiments. For example, in FIG. 5E, the waveform includes a ramp-up time period. In FIG. 5F, the waveform has a delivery duration that is switched to a non-delivery duration. An embodiment of FIG. 5F illustrates that the high-frequency oscillations may be generated to be present only during the delivery duration.

Referring now to FIGS. 6a, 6b and 6c and 7a and 7b, in various embodiments, a system 500 (also described herein as patch assembly 500) for iontophoretic transdermal delivery of various drugs and other therapeutic agents can comprise a skin conformable patch 505 and an electronics assembly 550. Patch 505 includes first and second electrode assemblies 510 and 512 which can correspond to one more embodiments of electrode assemblies described herein including embodiments corresponding to elements 110 and 112 and/or elements 210 and 212. The materials used to fabricate the electrode portions of the assemblies can include various corrosion resistant materials such as graphite further described in U.S. Provisional Patent Application Ser. No. 61/221,010 which is fully incorporated by reference herein for all purposes. Also, one or both of electrode assemblies 510 and 512 can include a pair 520 of tissue contacting ring shaped electrodes 521 and 522 concentrically spaced or otherwise arranged to reduce edge effects as is further described in U.S. Provisional Patent Application Ser. No. 61/224,453 which is fully incorporated by reference herein for all purposes.

Electronics assembly 550 typically includes a housing 560 which engages patch 505 so as to form patch assembly 500. Housing 560 includes a bottom and top surface 561 and 562 respectively, with the bottom surface 561 typically being the area of contact for engaging patch 505, though other arrangements are also contemplated. In particular embodiments, the housing 560 can be configured to be detachably coupled to patch 505 via one or more detachment elements 600.

Housing 560 can have a variety of shapes. In many embodiments, it can include a shaped contour 563 such as a curved shaped contour 564 (which can be for one or both of bottom surface 561 and top surface 562) that is configured to correspond to the contour C of the skin surface SS at the target tissue site TS where patch assembly 500 is placed such as the contour of the patients arm, leg or abdomen (e.g., on the front or side of the stomach including below the waist line so as to not be visible). Contours 563 and 564 may i) correspond to a standard contour for a particular target site; ii) may come in different sizes and shapes for different target tissue sites and sizes of patients; or iii) may be custom shaped for the particular patient and target tissue site. Also, the housing 560 can be conformable so as to at least partially conform to the contour C of the skin surface at the target tissue site TS where the patch 505 and housing 560 are placed (both when the patient is still and when he or she is moving resulting in bending movement and other deformation of the skin such that the skin surface contour is a flexing contour). Accordingly, in various embodiments, all or a portion of the housing can comprise various flexible polymers known in the art such as various elastomeric polymers, e.g., silicone and polyurethane. Other flexible polymers are also contemplated. The flexibility/conformability of the housing can also be configured to vary over the length of the housing to meet the needs of the particular target tissue site TS. For example, the housing can be configured to have the greatest amount of flexibility at its center portions 560c (which can be achieved in some embodiments by putting a crimp or articulated zone 560a near the center of the housing). Also, the flexibility profile of the housing 560 can be matched or otherwise correlated to the shape and flexibility profile of the patch 505. For example, in particular embodiments the flexibility/conformability of the housing can be configured for embodiments of the patch 505 having ring shaped electrodes 521 and 522. In these and related embodiments, housing 560 may have a structure which include areas 566 of greater flexibility (e.g., less stiffness) which may approximately align with ring shaped electrodes 521 and 522 (or others) such that the overall flexibility of the assembly 500 is not decreased over these areas. Areas 566 can have a shape which corresponds to the shape of electrodes 521 and 522 (or other shaped electrodes), though the size of the areas can be different from the size of the electrodes. Areas 566 can be achieved by decreasing the thickness of the housing in these areas and/or the use of more flexible materials. Other structures for housing 560 including shaped areas 566 are also contemplated, such as structures which have oval shapes areas 566 or even recessed areas 566.

Also in various embodiments, housing 560 can not only be conformable, but also have a profile 565 shaped and sized such that the entire patch assembly 500 can be worn beneath the user's clothing and can bend and flex sufficiently so that: i) it is not readily detached by pressure or force from the user's clothing (due to movement of the clothes and/or skin), allowing the patch assembly 500 stay on for extended periods when adhered to a tissue site underneath the user's clothes; and ii) is not readily visible beneath the user's clothes. In various embodiments, the profile 565 of the housing can have a contour 564 (of one or both of top and bottom surfaces 562 and 561) which corresponds to the contour C of the surface of the patient's arm, leg, abdomen or other target tissue site. Further, embodiments of the housing 560 can be sized, shaped and otherwise fabricated to bend and flex sufficiently to account for movement of the patient's skin when the patch assembly is placed on the patient's abdomen, arm, leg and other target tissue sites. In this way, even when placed under clothes (or not), the patch assembly can remain sufficiently adhered/attached to the patient's skin for an extended period of time so as to allow a desired dose of the drug or other therapeutic agent 102 to be delivered. In various embodiments, the time period can be up to 24 hours, up to three days, up to a week with even longer periods contemplated. Specific combinations of a patch 505 and housing 560 can be configured for specific desired attachment periods using one or more factors described herein (e.g., flexibility surface area, etc). For embodiments of the patch including elemental iron, such configurations can allow the patch to remain sufficiently adhered to the patient's skin for a sufficient time to deliver a therapeutic dose of elemental iron for the treatment of iron deficient anemia (e.g., 1 to 100 mg with specific embodiments of 20, 30 and 50 mg) at rates which facilitate uptake and utilization by the patient's iron metabolism. Similar configurations and methods can be employed for delivery of other drugs and therapeutic agents listed in Table 1.

Further, one or more of the size and shape (e.g., shape of the housing bottom surface 561 such as oval, circular, dogbone etc) and flexibility of the housing 560 can be selected relative to one or more of the size and shape (e.g., shape of patch surface 505s) and flexibility of patch 505 such that when the patch assembly 500 is worn openly or beneath the patient's clothes, the applied amount of force from the housing to the skin surface beneath the patch (due to movement of the patient's skin) or the clothing to the skin surface beneath the patch 505 (due to movement of the clothing or skin) is fairly uniform (e.g., there is an substantially uniform force distribution with minimal areas of force concentration). In use, these and related embodiments serve to minimize the amount of thermal, electrical or other injury to the skin from high current densities and/or hot spots from such force concentrations. Additionally for embodiments using dual point disbursement of therapeutic agent(s) 102 from embodiments of patch 505 having two more or electrode assemblies (e.g., electrode assemblies 110, and 112) such configurations minimizing force concentrations (from skin movement etc) also serve to minimize any effect on the delivery of therapeutic agent from the first electrode relative to the second electrode (or others). In particular embodiments, this can serve to minimize any effect on the delivery rate or total delivered amount of therapeutic agent from the first electrode relative to the second (or other electrodes).

In particular embodiments, such results can be achieved by matching the flexibility of the housing 560 to the patch 505 (either approximately equivalent or a selected amount higher or lower, e.g., 5 to 50%) as well as configuring the surface area of patch to be large enough relative to the surface area of the housing so as produce a snow-shoe like effect so as to evenly distribute any applied force to the housing from clothing or (other applied force such as that due to movement of the skin) over the entire surface area of the patch. Surface area ratios in the range of 1:1.5 to 1:10 (housing surface area to patch surface area) are contemplated, with specific embodiments of 1:2, 1:3, 1:5.

In still other embodiments, the housing 560 or patch 505 may include a pressures sensor 567, such as a solid state strain gauge which senses the amount of force applied by the user's clothes to the housing and or patch. Input from the pressure sensor can then be used to modulate (either increase or decrease) current delivered to the patch relative to the applied force. The current can be modulated down to prevent the development of hot spots on the patch from excessive pressure or modulated up to account for any increase in the electrical impedance of the skin due to the applied pressure.

Assembly 550 will typically include a power source 570 (also referred to herein as current source 570) and a controller 530 (e.g., a microprocessor) for controlling one or more aspects of the iontophoretic delivery of the agent to the skin. Controller 530 can also include an integrated or separate power controller 535 for controlling the delivery of current to the skin. One or both of the controllers 530 and 535 can be coupled to an H-bridge or other current switching/limiting device 540 for limiting or otherwise controlling the delivery of current to the skin. The housing will also typically include a cavity 580 for current source 570, such as a cylindrical shaped cavity which may be sized for standard size batteries such as AA or AAA batteries. Other shapes for cavity 580 are also contemplated.

In various embodiments, current source 570 can comprise one or more electrochemical batteries including an alkaline, lithium, lithium ion and like chemistries. For ease of discussion, current source 570 will be referred to herein as battery 570 but other current sources are equally applicable. Battery 570 can also comprise a rechargeable battery known in the art. The battery 570 can have a selected capacity to deliver sufficient current/voltage to the skin for transdermal delivery of the therapeutic agent for periods ranging from 2 to 24 hours or even longer. Power source 570 may also correspond to alternating power source 108 described herein. Accordingly, in embodiments including an electrochemical battery(s), power source 570 may include circuitry for converting a DC signal from the battery(s) into an AC signal. Other power/current sources 570 are also contemplated, such as various storage capacitors and piezo-electric based energy harvesting devices.

The patch 505 will typically include one or more conductive areas 506 for electrical coupling to conductive elements 591 on the electronics assembly 550. The conductive areas 506 can be coupled to conductive traces 590 placed on the patch surface 505s or within the patch 505. The conductive elements on the electronics assembly 550 can be coupled to one or both controllers and current source 570.

Detachment elements 600 can be spring loaded and can be configured to be engaged by the fingers of a user. In particular embodiments, detachment elements 600 may include or be mechanically coupled to one or more anchoring elements 601 such as a hook for anchoring into patch 505. The anchoring elements may also comprise adhesive areas placed on the housing bottom surface 561 which engage the patch surface 505S.

In use, detachment elements 600 allow the user to attach and detach an electronics assembly 550 to a selected patch 505. This allows the electronics assembly 550 to be reused for multiple patches. In an exemplary embodiment of using system 500, the user can obtain a particular patch 505, scan information about the patch using a bar code reader (or other indicia reading means) described below and then attach the patch 505 to the assembly 550. When the user is done using the patch (e.g., such as when the desired amount of drug has been delivered) the user then detaches assembly 550 from the patch 505 discarding the patch. In particular embodiments, assembly 550 can include programming which provides a signal such as beep or other alarm indicating to the user when to remove the patch 505. As an alternative, the patch surface 505s can include an indicator portion which changes color or otherwise provides visible indicia to the user when the required amount of agent has been delivered to the skin. In one embodiment, the indicia can comprise a symbol or marking that becomes visible when the amount of therapeutic agent has been delivered. Visibility of the marking can be due to depletion of therapeutic agent within the patch and/or a chemical or electrochemical reaction within or one the patch.

In particular embodiments, the electronics assembly 550 can also include a bar code reader for reading a bar code printed on the patch for ascertaining various information about the patch 505 including the type and amount of drug contained in the patch, a desired delivery regimen, lot numbers (of the patch and the therapeutic agent) shelf life, expiration date and related information. The patch may also contain a memory chip such as an EEPROM which contains similar information and is engaged by electronics assembly 550. Assembly 550 may also contain an EEPROM or other memory resource for storing information (described above). The EEPROM can couple to the microcontroller and can be programmed at the factory or by the doctor or pharmacist. This can be done directly or over a network such as the internet or cellular phone network or other like network. Other indicia reading means, for reading/detecting other indicia of information about patch 505 are also contemplated. Such indicia reading means can include without limitation use of various RF ID chips known in the art.

System 500 including patch 505 and assembly 550, can be sized and shaped to be placed in any number of locations on the patient's skin including the arm, leg or abdomen, back or other location. The particular material properties of the patch 505 and housing 560 (e.g., thickness, modulus of elasticity, bendability, etc) can also be so selected to allow placement at the desired location. For example, more flexible material properties can be selected for placement of the system over skin areas with greater amounts of bending by the user, such as the stomach. Also, patch 505 and assembly 550 can be packaged together, for example, as a kit 500k (which can include instructions for use) wherein the assembly 550 is matched to patch 505 in terms of size, current source, programming mechanical properties etc. Further, a given assembly 550 can be calibrated for such a group of patches 505 or patches 505 from a particular lot number. In such embodiments, multiple patches 505 can be included with a particular assembly 550. In use, this allows the patient to obtain a complete supply of patches to meet the delivery requirements for a particular therapeutic agent 102 over a period of days, weeks, or months. Further, the assembly 550 can be programmed such that when the patient is near the end of his or supply of patches, that the assembly will give the patient will a message to purchase more strips. In related embodiments, the assembly 550 can be configured to interface with the Internet and/or a mobile communication device such as cell phone, to send a message to the patient's pharmacy and/or doctor to do one or more of the following: i) renew the patient's prescription for a particular therapeutic agent patch 505; ii) have an order for a supple of the therapeutic agent patch 505 ready for the patient's pick up at his or her drug store; and/or iii) ship an order for the therapeutic agent patch to the patient's house.

Applications

Numerous applications exist for embodiments described herein. Table 1 lists, for example, various medical conditions that may be treated with various drugs and other active agents, using a system of electrode assemblies such as described above. The table further identifies whether the treatment can be patient activated, sensor activated, timed, or continuous. If patient activated, a user input mechanism 342 (FIG. 3) may be operated by the user when the electrode assemblies are in the deployed state to initiate operation of the electrode assemblies (and delivery of the active agent). Examples of user activated applications include delivery of various pain management drugs such as lidocaine or fentanyl. Sensor activated uses may incorporate use of one or more sensors 344 that interface with the user's body to determine whether a condition of the user requires treatment with the identified active agent. An example of a sensor activated application can include treatment of diabetes where the sensor is a blood glucose sensor or (other sensor means for detecting hyperglycemia) and administers a dose of insulin. A treatment is timed if it incorporates the timer 346 to determine when to start/stop the delivery durations.

TABLE 1

| Active Agent | Condition | Patient Activated | Sensor Activated | Timed | Continuous |
|---|---|---|---|---|---|
| Insulin | Diabetes | X | X | X | |
| GLP-1/Integrin | Diabetes | X | X | X | |
| $Fe^{2+}$ | Anemia | | | | X |
| Sodium (Na), Potassium (K) | Electrolyte renewal | | | | X |
| Furosemide | Epilepsy | | X | X | |
| Bumetanide | Migraine | X | X | X | |
| Aspirin | Inflammation | X | X | X | |
| Ketoprophin | Arthritis | X | | | |
| Lidocaine | Pain | X | | | |
| Fentanyl | Pain | X | | | |
| Alprazolin | Anxiety/Pain | X | X | | |
| Antibiotics | Wound Healing | | | | X |

In specific embodiments, the active agent can comprise a sufficient amount of elemental iron for the treatment of iron deficiency anemia . . . . The amount of elemental iron can be sufficient to provide between 1 to 100 mg of elemental iron to the patient for a period of days or even weeks. In various embodiments, the elemental iron can comprise ionic iron in the form of ferrous ($Fe^{2+}$) or ferric ($Fe^{3+}$) iron. The ionic iron can comprise an iron salt, a ferrous salt, a ferric salt, ferric pyrophosphate ferrous chloride or a combination thereof.

Although illustrative embodiments of the invention have been described in detail herein with reference to the accompanying drawings, it is to be understood that the invention is not limited to those precise embodiments. As such, many modifications and variations will be apparent to practitioners skilled in this art. Accordingly, it is intended that the scope of the invention be defined by the following claims and their equivalents. Furthermore, it is contemplated that a particular feature described either individually or as part of an embodiment can be combined with other individually described features, or parts of other embodiments, even if the other features and embodiments make no mentioned of the particular feature. This, the absence of describing combinations should not preclude the inventor from claiming rights to such combinations.

What is claimed is:

1. A patch assembly for iontophoretic transdermal delivery of a therapeutic agent to a patient, the assembly comprising:
   a conformable patch having two electrodes, the patch having a tissue contacting side including an adhesive and a non-tissue contacting side, each of the electrodes including a porous layer to allow for the iontophoretic transdermal delivery of the therapeutic agent to the patient through the tissue contacting side, each of the electrodes configured to hold a medium to contain the therapeutic agent;
   a housing having a top surface and a bottom surface, the bottom surface configured to engage the non tissue contacting side of the conformable patch;
   a current source positioned in or on the housing, the current source configured to deliver direct current;
   a power inverter coupled to the current source, the power inverter configured to convert direct current from the current source to alternating current; and a controller positioned in or on the housing and configured to receive an alternating current and cause dispersion of the therapeutic agent to alternate between electrodes;

wherein the housing has sufficient flexibility such that when the housing is engaged with the conformable patch to form the patch assembly, adhering the conformable patch to a target site on the patient's skin, the patch assembly has sufficient flexibility to deform with movement of the patient's skin so as to remain sufficiently adhered to the patient's skin over an extended period of time to transdermally deliver the agent.

2. The assembly of claim 1, where in the extended period of time is at least at day.

3. The assembly of claim 2, where in the extended period of time is at least three days.

4. The assembly of claim 3, where in the extended period of time is at least seven days.

5. The assembly of claim 1, further comprising at least one contact element positioned on the bottom surface of the housing for engaging and making electrical contact with the non tissue contacting side of the patch.

6. The assembly of claim 5, wherein, the contact element is operatively coupled to the controller.

7. The assembly of claim 1, wherein the housing includes at least one detachment element for mechanically disengaging the housing from the conformable patch.

8. The assembly of claim 7, wherein the detachment element is spring loaded.

9. The assembly of claim 1, wherein the controller comprises a first controller for controlling the delivery of the therapeutic agent and a second controller for controlling the delivery of current to the skin, where the first controller is configured to receive the alternating current and control the iontophoretic delivery of the therapeutic agent.

10. The assembly of claim 9, further comprising a current switching device operatively coupled to at least one of the first controller, the second controller or the current source.

11. The assembly of claim 10, wherein the current switching device comprises an H-bridge.

12. The assembly of claim 1, wherein the current source comprises an electrochemical battery, an alkaline battery, a lithium battery or a lithium-ion battery.

13. The assembly of claim 1, wherein the bottom surface of the housing has a curved contour.

14. The assembly of claim 13, wherein the curved contour corresponds to the contour of an arm, a leg or an abdomen.

15. The assembly of claim 1, wherein the housing has a profile shaped and sized to allow the patch assembly to be worn underneath the patient's clothing without substantially detaching from the patient's skin from movement of the patient's clothing or skin.

16. The assembly of claim 1, wherein the housing is conformable to a flexing contour of the patient's skin to allow the patch assembly to remain adhered to patient's skin over the extended period of time.

17. The assembly of claim 16, wherein the housing is conformable to a flexing contour of the patient's abdomen.

18. The assembly of claim 1, wherein the housing comprises a resilient polymer or an elastomer.

19. The assembly of claim 1, further comprising an input mechanism operatively coupled to the current source, the input mechanism configured to enable the patient to turn the current source on and off.

20. The assembly of claim 1, further comprising a bio-sensor coupled to the controller, the bio-sensor configured to detect a medical characteristic of the patient, wherein the controller controls the iontophoretic delivery of the therapeutic agent based on the medical characteristic.

21. The assembly of claim 1, wherein the housing has a flexibility to allow the patch assembly to deform with movement of the patient's skin.

22. The assembly of claim 1, wherein the housing includes one or more zones of increased flexibility which approximately align with at least one of the electrodes of the conformable patch.

23. The assembly of claim 1, wherein the housing is configured to allow the patch assembly to deform with movement of the patient's skin so as to not substantially affect the delivery of the therapeutic agent from the at least one electrode which is configured to hold the medium to contain the therapeutic agent as a result of forces from movement of the skin.

24. The assembly of claim 23, wherein the housing has a flexibility configured to allow the patch assembly to deform with movement of the patient's skin so as to not substantially affect the rate or total amount of delivery of the therapeutic agent from the at least one electrode which is configured to hold the medium to contain the therapeutic agent as a result of forces from movement of the skin.

25. The assembly of claim 1, wherein the therapeutic agent comprises elemental iron for treatment of iron deficient anemia.

26. The assembly of claim 25, wherein the patch assembly remains sufficiently adhered to the patient's skin for a sufficient period of time so as to transdermally deliver a therapeutic dose of elemental iron for the treatment of iron deficient anemia.

27. The assembly of claim 26, wherein the therapeutic dose of elemental iron is in the range of about 1 to about 100 mg.

28. The assembly of claim 1, wherein causing dispersion of the therapeutic agent to alternate between electrodes enables continuous transdermal delivery of the therapeutic agent using alternating points of the patient's skin to avoid skin irritation or saturation.

* * * * *